United States Patent [19]

Yokoo et al.

[11] Patent Number: 4,937,332

[45] Date of Patent: Jun. 26, 1990

[54] CEPHALOSPORIN DERIVATIVES

[75] Inventors: Chihiro Yokoo, Gyoda; Akira Onodera, Kuki; Hiroshi Fukushima, Saitama; Yoshiaki Watanabe, Kodaira; Kaoru Sota, Tokorozawa, all of Japan

[73] Assignee: Taisho Pharmaceutical Co., Ltd., Japan

[21] Appl. No.: 286,171

[22] Filed: Dec. 19, 1988

[30] Foreign Application Priority Data

Dec. 25, 1987 [JP] Japan ................. 62-329001

[51] Int. Cl.$^5$ .................. C07D 501/36; A61K 31/545
[52] U.S. Cl. .................................... 540/227
[58] Field of Search ................. 540/227; 514/206

[56] References Cited

U.S. PATENT DOCUMENTS 4,699,981 10/1987 Watanabe et al. ............... 548/226
4,758,556 7/1988 Dürkhemer et al. ............. 540/227

Primary Examiner—Nicholas S. Rizzo
Attorney, Agent, or Firm—Lorusso & Loud

[57] ABSTRACT

A cephalosporin derivative represented by the general formula

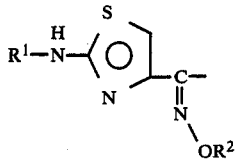

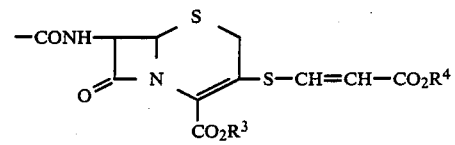

wherein $R^1$ is a hydrogen atom or a protecting group of the amino group, $R^2$ is a hydrogen atom or a protecting group of the hydroxyl group, $R^3$ is a hydrogen atom or a protecting group of the carboxyl group, and $R^4$ is a hydrogen atom or an alkyl group having 1 to 4 carbon atoms, and the non-toxic salts thereof are useful as antibacterial agents.

1 Claim, No Drawings

4,937,332

CEPHALOSPORIN DERIVATIVES

BACKGROUND OF THE INVENTION (1) Field of the Invention

The present invention relates to cephalosporin derivatives and their non-toxic salts having excellent antibacterial activity and good oral absorptivity.

(2) Prior Art

Orally absorbable cephalosporin compounds having a 2-carboxymethoxyimino-2-(2-aminothiazol-4-yl)acetamido group at the 7-position of the cephem nucleus are known in U.S. Pat. No. 4,699,981. In addition, among cephalosporin drugs used clinically for oral administration are cephalexin, cefachlor, cefixime and the like. However, these oral cephalosporin drugs are much inferior to the cephalosporin drugs developed recently for injectional administration in terms of antibacterial activity and antibacterial spectrum against various pathogenic bacteria.

Under such circumstances, it is desired to discover new oral cephalosporin drugs having stronger antibacterial activity and wider antibacterial spectrum.

SUMMARY OF THE INVENTION

As a result of the intensive research, the present inventors have discovered novel orally absorbable cephalosporin derivatives showing stronger antibacterial activity and wider antibacterial spectrum than the prior art oral cephalosporin drugs, and completed the present invention.

An object of the present invention is to provide a cephalosporin derivative represented by the formula

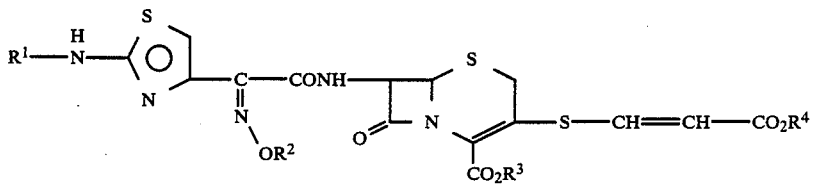

(I)

wherein $R^1$ is a hydrogen atom or a protecting group of the amino group, $R^2$ is a hydrogen atom or a protecting group of the hydroxyl group, $R^3$ is a hydrogen atom or a protecting group of the carboxyl group, and $R^4$ is a hydrogen atom or an alkyl group having 1 to 4 carbon atoms, and the non toxic salts thereof.

DETAILED DESCRIPTION OF THE INVENTION

In the present invention, the protecting groups of the amino group, hydroxyl group and carboxyl group are those frequently used in the field of the β-lactam chemistry. For example, the protecting groups of the amino group for $R^1$ may be a trityl group, a monochloroacetyl group, a formyl group, a benzyloxycarbonyl group, a 4-nitrobenzyloxycarbonyl group, a 4-methoxybenzyloxycarbonyl group, a t-butoxycarbonyl group, a trimethylsilyl group and the like, the protecting groups of the hydroxyl group for $R^2$ may be a formyl group, an acetyl group, a propionyl group, a methoxycarbonyl group, an ethoxycarbonyl group, a butoxycarbonyl group, a t-butoxycarbonyl group, a benzoyl group, a toluoyl group, a benzenesulfonyl group, a tosyl group, a phenylacetyl group, a 4-methoxybenzyl group, 2,4-dimethoxybenzyl group, a trityl group, a tetrahydropyranyl group and the like. The protecting groups of the carboxyl group for $R^3$ may be a methyl group, an ethyl group, a propyl group, an isopropyl group, a butyl group, an isobutyl group, a t-butyl group, a vinyl group, an allyl group, an ethynyl group, a methoxymethyl group, an ethoxymethyl group, a 1-methoxyethyl group, a methylthiomethyl group, a methylthioethyl group, a carboxymethyl group, a carboxyethyl group, a t-butoxycarbonylmethyl group, a 2-(t-butoxycarbonyl)ethyl group, a benzyl group, a 4-nitrobenzyl group, a 4-methoxybenzyl group, a benzhydryl group, a bis-(4-methoxyphehyl)methyl group, a 3,4-dimethoxybenzyl group, a trityl group, a phenethyl group, a phenacyl group, a 2,2,2-trichloroethyl group, a trimethylsilyl group, a 4-hydroxy-3,5-di(t-butyl)benzyl group, a phenyl group, a tolyl group, a xyryl group and groups known in the pro-drug techniques of the β-lactam drugs such as a 5-mehyl-1,3-dioxacyclopent-4-en-2-on-4-ylmethyl group, an acetoxymethyl group, a pivaloyloxymethyl group, a 1-pivaloyloxyethyl group, a 1 acetoxyethyl group, a 3-phthalidyl group, a 1-(cyclohexyloxycarbonyloxy)ethyl group, a 1-(isopropoxycarbonyloxy)ethyl group and the like.

The alkyl group having 1 to 4 carbon atoms for $R^4$ refers to a straight or branched chain alkyl group such as, for example, a methyl group, an ethyl group, a n-propyl group, an isopropyl group, a n butyl group, an isobutyl group and the like.

The non-toxic salt of the compound of Formula (I) of the present invention refers to pharmacologically acceptable salts, for example, salts with inorganic bases including sodium, potassium, magnesium and ammonium; salts with organic bases such as triethylamine, cyclohexylamine and the like; basic amino acids such as arginine, lysine and the like; and salts with mineral acids such as sulfuric acid, hydrochloric acid, phosphoric acid and the like; and salts with organic acids such as acetic acid, lactic acid, tartaric acid, fumaric acid, maleic acid, trifluoroacetic acid, methanesulfonic acid and the like.

Among the preferred compounds are compounds of Formula (I) wherein $R^1$ and $R^2$ are each a hydrogen atom, and $R^3$ is a hydrogen atom or a group known in the pro-drug techniques of the β-lactam drugs such as a pivaloyloxymethyl group and the like, and $R^4$ is a methyl group or an ethyl group.

The compounds of Formula (I) of the present invention are those in the forms of geometric isomers [E-form and Z-form] derived from the oxyimino group at the 7-position side chain and the vinyl group at the 3-position side chain, respectively, and both isomers are included within the scope of the present invention, but the Z-form derived from the oxyimino group at the 7-position side chain is preferred.

The compounds of Formula (I) of the present invention can be, for example, obtained according to the following synthetic methods [in the reaction scheme below, $R^1$ and $R^2$ are as defined above other than a hydrogen atom, $R^3$ and $R^4$ are as defined above, $R^5$ is a protecting group of the amino group such as a phenylacetyl group, a phenoxyacetyl group, a trityl group, a phthaloyl group, a formyl group or a benzoyl group, and $R^6$ is a hydrogen atom or a easily hydrolyzable group in the body which is known in the pro-drug techniques of the β-lactam drugs as described above for $R^3$, Y is a halogen atom (e.g., a chlorine atom, a bromine atom and an iodine atom), a methanesulfonyloxy group, a trifluoromethanesulfonyloxy group, a diphenylphosphoryloxy group or a p-toluenesulfonyloxy group].

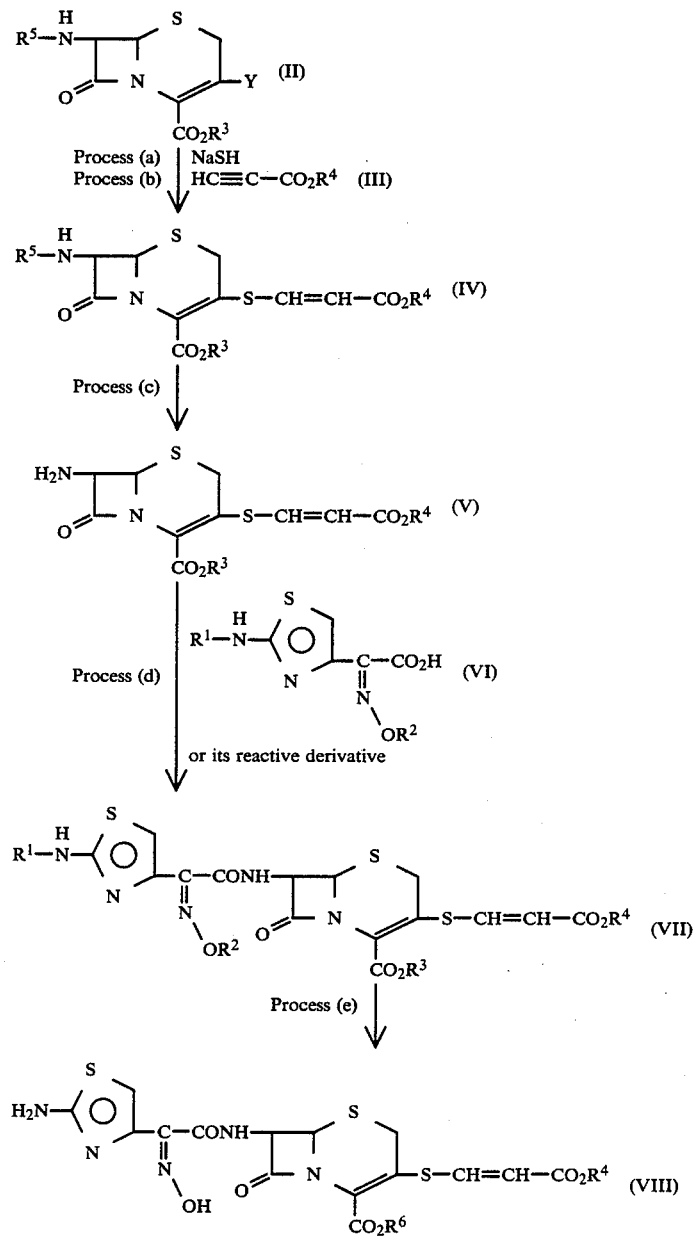

Process (a): A known compound of Formula (II) is dissolved in a reaction-inert organic solvent, and the solution together with 1.0 to 1.2 molar equivalents of sodium hydrosulfide in the presence of a base is stirred. The reaction temperature is from −50° C. to 100° C., preferably from −40° C. to 5° C. The reaction time is from 10 minutes to 4 hours, preferably from 10 minutes to one hour.

Process (b): To the resulting compound obtained in Process (a), after isolation or in the same reaction system without isolation, is added to 1.0 to 2.0 molar equivalents of the compound of Formula (III), and the mixture is stirred in the presence of a base at a reaction temperature of from −50° C. to 100° C., preferably from −25° C. to 50° C., to give a 3-thio substituted derivative of Formula (IV). The reaction time depends on the kind of the base used, the kind of the compound of Formula (III) used and the reaction temperature, but usually it is in the range of 10 minutes to 2 hours.

The preferred solvents in Processes (a) and (b) are N,N-dimethylformamide, N,N-dimethylacetamide, dimethyl sulfoxide, hexamethylphosphoramide, acetonitrile, tetrahydrofuran, dichloromethane and the like, and they are used alone or in admixture. The preferred bases are organic bases such as diisopropylethylamine, N,N-dimethylaminopyridine, N,N-dimethylaniline, triethylamine and the like. The most preferred amount of the base is from 0.2 to 1.5 molar equivalents relative to the compound of Formula (II).

Process (c): The protecting group at the 7-position of the compound of Formula (IV) obtained in Process (b) can be eliminated by a method frequently used in the field of the β-lactam chemistry to give the compound of Formula (V). For example, a compound of Formula IV wherein the protecting group $R^1$ is a phenoxyacetyl group, a phenylacetyl group or a benzoyl group is dissolved in dichloromethane or benzene, and 1.5 to 2.0 molar equivalents of phosphorus pentachloride and 2.0 to 3.0 molar equivalents of pyridine are added, and then the mixture is stirred at $-40°$ C. to 30° C. for 30 minutes to 3 hours. Subsequently, a large excess amount of methanol is added at $-50°$ C. to 20° C., and the mixture is stirred for 30 minutes to 2 hours. After addition of a large excess amount of water, the mixture is stirred at $-50°$ C. to 20° C. for 30 minutes to 1 hour to give the compound of Formula (V).

A compound of Formula (IV) wherein the protecting group $R^5$ is a trityl group is dissolved in a reaction-inert solvent (e.g., ethyl acetate), 1.0 to 1.5 molar equivalents of p-toluenesulfonic acid monohydrate is added under ice-cooling, and then the mixture is stirred for 1 to 5 hours to give the compound of Formula (V) in the form of p-toluenesulfonic acid salt. If necessary, the p-toluenesulfonic acid salt is treated with a base to give the compound of Formula (V) in the form of the free base.

Process (d): In order to obtain the compound of Formula (VII) from the compound of Formula (V), the compound of Formula (V) is reacted with a 2-aminothiazoleacetic acid derivative of Formula (VI) in the presence of a condensing agent or reacted with a reactive derivative of the compound of Formula (VI). Examples of the condensing agent are N,N'-dicyclohexylcarbodiimide, 1-ethoxycarbonyl-2-ethoxy-1,2-dihydroquinoline, carbonyldiimidazole, diphenylphosphoryl azide, Vilsmeier reagent and the like. Examples of the reactive derivative of the compound of Formula (VI) are the acid halides (e.g., acid chloride and acid bromide), acid anhydrides (e.g., symmetrical acid anhydrides of the compound of Formula (VI), and mixed acid anhydrides with ethyl chlorocarbonate, diphenylphosphoric acid, methanesulfonic acid and the like), and activated esters (e.g., esters with 4-nitrophenol, thiophenol, N-hydroxysuccinimide and the like).

Referring to the use of a mixed acid anhydride of the compound of Formula (VI) with methanesulfonic acid as a reactive derivative of the compound of Formula (VI), first the compound of Formula (VI) is dissolved in a reaction-inert solvent and then 1.0 to 1.1 molar equivalents of methanesulfonyl chloride is added to the solution in the presence of a base at $-70°$ C. to $-30°$ C., and the mixture is stirred for 20 to 40 minutes to prepare a mixed acid anhydride of the compound of Formula (VI). To the reaction mixture is added a solution of 0.5 to 0.7 molar equivalent of the compound of Formula (V) in the presence of a base at a temperature of from $-70°$ C. to $-30°$ C., and the mixture is stirred for 20 to 40 minutes to give the compound of Formula (VII). Preferred solvents in this process are N,N-dimethylformamide, tetrahydrofuran, acetonitrile, dichloromethane, chloroform and the like. Preferred bases are N,N-diisopropylethylamine, triethylamine, N,N-dimethylaniline, N,N-dimethylaminopyridine, pyridine and the like. The amount of the base used is 1.0 to 2.2 molar equivalents relative to the compound of Formula (V).

When used an acid chloride as a reactive derivative of the compound of Formula (VI), first the compound of Formula (VI) is dissolved in a reaction-inert solvent and then 1.0 to 1.1 molar equivalents of phosphorus pentachloride is added to the solution in the presence of a base at $-30°$ C. to $-10°$ C., and the mixture is stirred for 10 to 30 minutes to prepare an acid chloride of the compound of Formula (VI). To the reaction mixture is added a solution of 0.7 to 1.0 molar equivalent of the compound of Formula (V) in the same reaction-inert solvent as those mentioned above at a temperature ranging from $-30°$ C. to 0° C., and the mixture is stirred for 10 to 30 minutes to give the compound of Formula (VII). Preferred solvents in this process are dichloromethane, chloroform, acetonitrile, N,N-dimethylformamide and the like. Preferred bases are pyridine, triethylamine, N,N-dimethylaminopyridine, N,N-dimethylaniline, diisopropylethylamine and the like. The amount of the base used is 4.0 to 5.5 molar equivalents relative to the compound of Formula (V).

Process (e): In order to obtain the compound of Formula (VIII) from the compound of Formula (VII), the protecting groups of the compound of Formula (VII) are eliminated by hydrolysis or reduction frequently used in the field of the β-lactam chemistry.

Hydrolysis is preferably carried out in the presence of an acid. Examples of the acid are inorganic acids such as hydrochloric acid, hydrobromic acid, sulfuric acid and the like, organic acids such as formic acid, acetic acid, trifluoroacetic acid, methanesulfonic acid, benzenesulfonic acid, p-toluenesulfonic acid and the like. Lewis acids such as boron trifluoride, boron trifluoride etherate, alminium trichloride, antimony pentachloride, ferric chloride, stannic chloride, titanium tetrachloride, zinc chloride and the like and acidic ion exchange resins can be used instead of the acid described above. Furthermore, when the above organic acid or Lewis acid is used, hydrolysis is preferably carried out in the presence of a cation trapping agent such as anisole. Examples of the preferred solvent in hydrolysis are water, methanol, ethanol, tetrahydrofuran, N,N-dimethylformamide, dioxane, dichloromethane, nitromethane and the like. When the acid described above is liquid, it can itself be used as a solvent.

Reduction may be carried out by a method of chemical reduction and catalytic reduction. Reducing agents used in the chemical reduction may be a combination of a metal such as zinc, iron and the like, with an organic or inorganic acid such as formic acid, acetic acid, trifluoroacetic acid, hydrochloric acid, hydrobromic acid and the like.

Examples of the catalyst used in the catalytic reduction are platinum black, platinum oxide, palladium black, palladium on carbon, Raney nickel and the like.

Usually, reduction may be carried out in a conventional solvent which is unaffected disadvantageously to the reaction such as water, methanol, ethanol, acetic acid, tetrahydrofuran, N,N-dimethylformamide, dioxane and a mixture thereof.

The reaction temperature of the above hydrolysis or reduction is not restricted, but usually the reaction is carried out under cooling or warming.

The compounds of Formula (I) and their non-toxic salts of the present invention show not only strong antibacterial activity against various pathogenic bacteria containing gram positive bacteria and gram negative bacteria, but also excellent oral absorption, therefore, they are useful as antibacterial agents for oral administration.

For the purposes, the compound of the present invention may be administered orally in a conventional form such as tablets, pills, capsules, granules and the like, all of which can be prepared according to conventional pharmaceutical practices. In the above preparations are used conventional additives such as fillers, binding agents, disintegrators, pH adjusting agents, solubilizers and the like.

The dosage of the compound of the present invention depends on the age of the patient and the kind and conditions of the disease, but usually it is from 10 to 3000 mg in single or several divided doses per day.

Subsequently, the results of the antibacterial activity test and oral absorption test of the compounds of the present invention are shown below.

Experiment 1

The antibacterial activity against various bacteria was measured by the agar plate dilution method (inoculum size $10^6$ cells/ml), and the results are shown in the following Table 1.

TABLE 1

| Bacteria | Minimum Inhibitory Concentration (μg/ml) Test compound | | | |
|---|---|---|---|---|
| | A | B | C | D |
| Staphylococcus aureus 209P-JC | 0.2 | 0.78 | 12.5 | 6.25 |
| Staphylococcus aureus K-1 | 3.13 | >100 | >100 | — |
| Escherichia coli NIJH JC-2 | ≦0.025 | 3.13 | 0.05 | 0.05 |
| Escherichia coli A13 | 6.25 | >100 | >100 | >100 |
| Klebsiella pneumoniae T-25 | 0.2 | 100 | 12.5 | 0.39 |
| Morganella morganii IID 602 | 0.05 | >100 | 0.39 | 0.25 |

Note
A: 7β-{2-(2-aminothiazol-4-yl)-2-[(Z)-hydroxyimino]acetamido}-3-[(Z)-2-methoxycarbonylvinylthio]-3-cephem-4-carboxylic acid sodium salt [shown in Example 1(e)]
B: Cephalexin (known compound)
C: Cefixime sodium salt (known compound)
D: 7β-{2-(2-aminothiazol-4-yl)-2-[(Z)-carboxymethoxyimino]acetamido}-3-[(Z)-methoxycarbonylvinylthio]-3-cephem-4-carboxylic acid sodium salt (known compound)

Experiment 2

Three male wister rats (7 weeks old) for each group were administered orally with the test compounds, and the change of the concentration of the compound in blood was measured.

Dosage of the test compound:
  50 mg/kg (suspended in 5% gum arabic)
Quantitative method: Bioasssay
  (test bacterium: *Escherichia coil* SC507)
The results are shown in Table 2.

TABLE 2

| Time after administration | Concentration in blood (μg/ml) Test compound | |
|---|---|---|
| | A | B |
| One Hour | 11.02 | 14.32 |
| Two Hours | 14.24 | 13.73 |
| Four Hours | 16.91 | 4.78 |

Note
A: 7β-{2-(2-aminothiazol-4-yl)-2-[(Z)-hydroxyimino]acetamido}-3-[(Z)-2-methoxycarbonylvinylthio]-3-cephem-4-carboxylic acid sodium salt [shown in Example 1(e)]
B: Cephalexin (known compound)

The present invention is illustrated by the following Examples in more detail.

Example 1

(a) To a solution of 34.4 g (64.5 mM) of 4-methoxybenzyl 7β-phenylacetamido-3-methanesulfonyloxy-3-cephem-4-carboxylate in 100 ml of N,N-dimethylformamide were added at −30° C. a solution of 5.68 g (71.0 mM) of 70% sodium hydrosulfide in 50 ml of N,N-dimethylformamide and 12.5 g (96.9 mM) of diisopropylethylamine, and the mixture was stirred for 30 minutes. After the reaction, 500 ml of water was added and the mixture was washed with 300 ml of ethyl acetate. The aqueous layer was adjusted to pH 2 to 3 with 0.5% hydrochloric acid and extracted with 1 l of ethyl acetate, and the extract was washed with a saturated aqueous sodium chloride solution (300 ml×3) and dried over anhydrous magnesium sulfate. The solvent was evaporate and n-hexane was added to the residue for powdering to give 22.0 g of 4-methoxyphenyl 7β-phenylacetamido-3-mercapto-3-cephem-4-carboxylate.

NMR (CDCl$_3$) δ(ppm);
  3.32 (1H, d, J=18 Hz)
  3.46 (1H, d, J=18 Hz)
  3.62 (2H, s)
  3.78 (3H, s)
  4.98 (1H, d, J=5 Hz)
  5.18 (2H, s)
  5.35 (1H, s)
  5.63 (1H, dd, J=5 Hz, 9 Hz)
  6.42 (1H, d, J=9 Hz)
  6.88 (2H, d, J=8 Hz)
  7.20–7.40 (7H, m)
IR$\nu_{max}^{KBr}$cm$^{-1}$;
  3250, 1760, 1650, 1510, 1350, 1230, 1170

(b) To a solution of 22.0 g (46.8 mM) of 4-methoxybenzyl 7β-phenylacetamido-3-mercapto-3-cephem-4-carboxylate, obtained in the above (a), in 150 ml of N,N-dimethylformamide were added at −20° C. 5.89 g (70.1 mM) of methyl propiolate and 1.81 g (14 mM) of diisopropylethylamine, and the mixture was stirred for 30 minutes. After the reaction, 300 ml of 0.5% hydrochloric acid was added, the mixture was extracted with 700 ml of ethyl acetate, and the extract was washed with of a saturated aqueous sodium chloride solution (300 ml×3) and dried over anhydrous magnesium sulfate. The solvent was evaporated, and diethyl ether was added to the residue for powdering to give 16.2 g of 4-methoxybenzyl 7β-phenylacetamido-3-[(Z)-2-methoxycarbonylvinylthio]-3-cephem-4-carboxylate.

NMR (CDCl$_3$) δ(ppm);
  3.44 (1H, d, J=18 Hz)
  3.64 (2H, s)
  3.74 (1H, d, J=18 Hz)
  3.76 (3H, s)
  3.79 (3H, s)
  4.98 (1H, d, J=5 Hz)
  5.21 (2H, s)

5.84 (1H, dd, J=5 Hz, 9 Hz)
5.90 (1H, d, J=10 Hz)
6.31 (1H, d, J=9 Hz)
6.86 (2H, d, J=8 Hz)
6.95 (1H, d, J=10 Hz)
7.24-7.44 (7H, m)
IR$\nu_{max}^{KBr}$cm$^{-1}$;
3250, 1780, 1690, 1510, 1355, 1220, 1165

(c) To a cooled (0° C.) solution of 18.3 g (33.0 mM) of 4-methoxybenzyl 7β-phenylacetamido-3-[(Z)-2-methoxycarbonylvinylthio]-3-cephem-4-carboxylate in 200 ml of dry dichloromethane were added 7.82 g (99.0 mM) of pyridine and 13.7 g (65.8 mM) of phosphorus pentachloride, and the reaction temperature was raised to room temperature for a period of 30 minutes, and the mixture was stirred at the same temperature for 1 hour. To the cooled (−50° C.) reaction solution was added 100 ml of dry methanol, and the mixture was stirred at −20° C. for 1 hour. Upon continued cooling of the reaction mixture to −50° C., 100 ml of water was added, and the mixture was stirred under ice-cooling for 40 minutes. The mixture was made weakly basic by addition of a saturated aqueous sodium bicarbonate solution, and extracted with 300 ml of ethyl acetate, and the extract was washed with 200 ml of a saturated aqueous sodium chloride solution and dried over anhydrous magnesium sulfate. The solvent was evaporated, and diethyl ether was added to the residue for powdering to give 10.6 g of 4-methoxybenzyl 7β-amino-3-[(Z)-2-methoxycarbonylvinylthio]-3-cephem-4-carboxylate.

NMR (CDCl$_3$) δ(ppm);
1.71 (2H, s)
3.48 (1H, d, J=18 Hz)
3.78 (3H, s)
3.80 (1H, d, J=18 Hz)
3.81 (3H, s)
4.79 (1H, d, J=5 Hz)
4.99 (1H, d, J=5 Hz)
5.25 (2H, s)
5.90 (1H, d, J=10 Hz)
6.87 (2H, d, J=8 Hz)
6.97 (1H, d, J=10 Hz)
7.34 (2H, d, J=8 Hz)
IR$\nu_{max}^{KBr}$cm$^{-1}$;
3320, 1755, 1705, 1690, 1610, 1510, 1345, 1220, 1165

(d) To a solution of 531 mg (0.92 mM) of 2-(2-tritylaminothiazol-4-yl)-2-[(Z)-2,4-dimethoxybenzyloxyimino]acetic acid in 10 ml of N,N-dimethylformamide was added 124 mg (0.96 mM) of diisopropylethylamine. To the cooled (−50° C.) mixture was added 105 mg (0.92 mm) of methanesulfonyl chloride, and the mixture was stirred for 30 minutes. Then, 200 mg (0.46 mM) of 4-methoxybenzyl 7β-amino-3-[(Z)-2-methoxycarbonylvinylthio]-3-cephem-4-carboxylate and 60 mg (0.46 mM) of diisopropylethylamine were added at the same temperature, and the mixture was stirred for 30 minutes. After the reaction, 30 ml of water was added, the mixture was extracted with 50 ml of ethyl acetate, and the extract was washed with 30 ml of a saturated aqueous sodium chloride solution and dried over anhydrous magnesium sulfate. The solvent was evaporated and the residue was chromatographed on silica gel column (eluent; ethyl acetate:benzene=1:4) to give 270 mg of 4-methoxybenzyl 7β-{2-(2-tritylaminothiazol-4-yl)-2-[(Z)-2,4-dimethoxybenzyloxyimino]acetamido}-3-[(Z)-2-methoxycarbonylvinylthio]-3-cephem-4-carboxylate.

NMR (CDCl$_3$) δ(ppm);
3.12 (1H, d, J=17 Hz)
3.60 (1H, d, J=17 Hz)
3.70 (3H, s)
3.75 (3H, s)
3.77 (3H, s)
3.80 (3H, s)
3.94 (1H, d, J=5 Hz)
5.22 (2H, s)
5.23 (1H, d, J=10 Hz)
5.34 (1H, d, J=10 Hz)
5.81 (1H, dd, J=5 Hz, 9 Hz)
5.94 (1H, d, J=10 Hz)
6.35-6.47 (2H, m)
6.83 (1H, s)
6.86 (2H, d, J=8 Hz)
6.93 (1H, d, J=10 Hz)
6.98 (1H, bs)
7.20-7.40 (19H, m)
IR$\nu_{max}^{KBr}$cm$^{-1}$;
3380, 1790, 1700, 1615, 1590, 1515, 1480, 1360, 1290, 1220, 1160, 1115, 1035

(e) To a mixture of 3.5 ml of trifluoroacetic acid and 0.7 ml of anisole was added under ice-cooling 250 mg (0.25 mM) of 4-methoxybenzyl 7β-{2-(2-tritylaminothiazol-4-yl)-2-[(Z)-2,4-dimethoxybenzyloxyimino]acetamido}-3-[(Z)-2-methoxycarbonylvinylthio]-3-cephem-4-carboxylate, and the mixture was stirred for 40 minutes and then at room temperature for 10 minutes. After the reaction, the reaction solution was slowly added dropwise to a mixture of diethyl ether and n-hexane (1:2, 30 ml), and the formed crystals were collected by filtration to give 150 mg of 7β-{2-(2-aminothiazol-4-yl)-2-[(Z)-hydroxyimino]acetamido}-3-[(Z)-2-methoxycarbonylvinylthio]-3-cephem-4-carboxylic acid trifluoroacetate.

Then, of the crystals and 43 mg (0.51 mM) of sodium bicarbonate were dissolved in 4 ml of water, and the solution was chromatographed on Sephadex LH-20 column (eluent; water) to give 120 mg of 7β-{2-(2-aminothiazol-4-yl)-2-[(Z)-hydroxyimino]acetamido}-3-[(Z)-2-methoxycarbonylvinylthio]-3-cephem-4-carboxylic acid sodium salt.

NMR (D$_2$O) δ(ppm);
3.57 (1H, d, J=17 Hz)
3.77 (3H, s)
3.97 (1H, d, J=17 Hz)
5.32 (1H, d, J=5 Hz)
5.89 (1H, d, J=5 Hz)
6.04 (1H, d, J=10 Hz)
7.00 (1H, s)
7.32 (1H, d, J=10 Hz)
IR$\nu_{max}^{KBr}$cm$^{-1}$;
3260, 1765, 1675, 1610, 1525, 1390, 1355, 1230, 1200, 1175, 1135

Then, a solution of 120 mg of the sodium salt obtained in the above in 5 ml of water was adjusted to pH 2.5 by the addition of 10% hydrochloric acid under ice-cooling, and the formed crystals were collected by filtration to give 80 mg of 7β-{2-(2-aminothiazol-4-yl)-2-[(Z)-hydroxyimino]acetamido}-3-[(Z)-2-methoxycarbonylvinylthio]-3-cephem-4-carboxylic acid.

NMR (DMSO-d$_6$) δ(ppm);
3.66 (3H, s)
3.67 (1H, d, J=17 Hz)
4.06 (1H, d, J=17 Hz)
5.20 (1H, d, J=5 Hz)
5.83 (1H, dd, J=5 Hz, 8 Hz)
6.03 (1H, d, J=10 Hz)
6.67 (1H, s)

7.14 (2H, bs)
7.51 (1H, d, J=10 Hz)
9.52 (1H, d, 8 Hz)
11.33 (1H, s)
IR$\nu_{max}^{KBr}$cm$^{-1}$;

3345, 1775, 1675, 1630, 1435, 1390, 1360, 1230, 1175, 1005

Following the procedures and reaction conditions of Example 1(b), there were obtained the following compounds shown in Table 3.

In the following Tables, G is a phenylacetamido group, DMB is a 2,4-dimethoxybenzyl group, Tr is a trityl group, PMB is a 4-methoxybenzyl group, Bh is a benzhydryl group, and POM is a pivaroyloxymethyl group.

TABLE 3

| Example No. | R$^3$ | R$^4$ | NMR(CDCl$_3$) δ(ppm) | IR $\nu_{max}^{KBr}$ cm$^{-1}$ |
|---|---|---|---|---|
| 2(b) | —PMB | —CH(CH$_3$)$_2$ | 1.27(3H, d, J=6Hz) | 3270 |
| | | | 1.29(3H, d, J=6Hz) | 2980 |
| | | | 3.42(1H, d, J=18Hz) | 1780 |
| | | | 3.60(1H, d, J=16Hz) | 1720 |
| | | | 3.69(1H, d, J=16Hz) | 1695 |
| | | | 3.74(1H, d, J=18Hz) | 1655 |
| | | | 3.80(3H, s) | 1615 |
| | | | 4.97(1H, d, J=5Hz) | 1585 |
| | | | 4.98-5.18(1H, m) | 1530 |
| | | | 5.20(2H, s) | 1515 |
| | | | 5.74(1H, dd, J=5Hz, 9Hz) | 1370 |
| | | | 5.76(1H, d, J=10Hz) | 1225 |
| | | | 6.08(1H, d, J=9Hz) | 1175 |
| | | | 6.86(2H, d, J=8Hz) | 1110 |
| | | | 6.89(1H, d, J=10Hz) | |
| | | | 7.23-7.42(7H, m) | |
| 3(b) | —PMB | —Bh | 3.40(1H, d, J=18Hz) | 3360 |
| | | | 3.59(1H, d, J=16Hz) | 2935 |
| | | | 3.68(1H, d, J=16Hz) | 1775 |
| | | | 3.73(1H, d, J=18Hz) | 1715 |
| | | | 3.74(3H, s) | 1690 |
| | | | 4.97(1H, d, J=5Hz) | 1660 |
| | | | 5.13(1H, d, J=12Hz) | 1615 |
| | | | 5.20(1H, d, J=12Hz) | 1575 |
| | | | 5.83(1H, dd, J=5Hz, 9Hz) | 1515 |
| | | | 6.02(1H, d, J=10Hz) | 1390 |
| | | | 6.03(1H, d, J=9Hz) | 1365 |
| | | | 6.78(2H, d, J=8Hz) | 1285 |
| | | | 6.97(1H, d, J=10Hz) | 1255 |
| | | | 6.98(1H, s) | 1225 |
| | | | 7.20-7.42(17H, m) | 1175 |
| | | | | 1035 |
| 4(b) | —POM | —CH$_3$ | 1.20(9H, s) | 3290 |
| | | | 3.47(1H, d, J=18Hz) | 1785 |
| | | | 3.60(1H, d, J=16Hz) | 1755 |
| | | | 3.70(1H, d, J=16Hz) | 1365 |
| | | | 3.75(3H, s) | 1225 |
| | | | 3.79(1H, d, J=18Hz) | 1170 |
| | | | 5.01(1H, d, J=5Hz) | 1110 |
| | | | 5.83(1H, d, J=6Hz) | |
| | | | 5.85(1H, dd, J=5Hz, 9Hz) | |
| | | | 5.89(1H, d, J=6Hz) | |
| | | | 5.99(1H, d, J=10Hz) | |
| | | | 6.12(1H, d, J=9Hz) | |
| | | | 6.98(1H, d, J=10Hz) | |
| | | | 7.23-7.44(5H, m) | |

Following the procedures and reaction conditions of Example 1(c) using the compounds obtained in Examples 2(b) to 4(b) of Table 3, there were obtained the corresponding compounds shown in Table 4.

TABLE 4

| Example No. | R$^3$ | R$^4$ | NMR(CDCl$_3$) δ(ppm) | IR $\nu_{max}^{KBr}$ cm$^{-1}$ |
|---|---|---|---|---|
| 2(c) | —PMB | —CH(CH$_3$)$_2$ | 1.28(3H, d, J=6Hz) | 3400 |

TABLE 4-continued

[Structure: H2N-β-lactam-S-CH2-C(=)-S-CH=CH-CO2R4 with CO2R3]

| Example No. | R³ | R⁴ | NMR(CDCl₃) δ(ppm) | IR $\nu_{max}^{KBr}$ cm⁻¹ |
|---|---|---|---|---|
|  |  |  | 1.30(3H, d, J=6Hz) | 2980 |
|  |  |  | 1.72(2H, bs) | 1780 |
|  |  |  | 3.48(1H, d, J=18Hz) | 1725 |
|  |  |  | 3.79(1H, d, J=18Hz) | 1690 |
|  |  |  | 3.80(3H, s) | 1615 |
|  |  |  | 4.78(1H, d, J=5Hz) | 1575 |
|  |  |  | 4.97(1H, d, J=5Hz) | 1515 |
|  |  |  | 5.00–5.19(1H, m) | 1375 |
|  |  |  | 5.23(2H, s) | 1350 |
|  |  |  | 5.86(1H, d, J=10Hz) | 1225 |
|  |  |  | 6.86(2H, d, J=8Hz) | 1175 |
|  |  |  | 6.93(1H, d, J=10Hz) | 1105 |
|  |  |  | 7.33(1H, d, J=8Hz) |  |
| 3(c) | —PMB | —Bh | 1.65(2H, s) | 3410 |
|  |  |  | 3.47(1H, d, J=18Hz) | 2935 |
|  |  |  | 3.74(3H, s) | 1765 |
|  |  |  | 3.78(1H, d, J=18Hz) | 1720 |
|  |  |  | 4.77(1H, d, J=5Hz) | 1700 |
|  |  |  | 4.97(1H, d, J=5Hz) | 1615 |
|  |  |  | 5.17(1H, d, J=11Hz) | 1515 |
|  |  |  | 5.23(1H, d, J=11Hz) | 1455 |
|  |  |  | 6.02(1H, d, J=10Hz) | 1390 |
|  |  |  | 6.79(2H, d, J=8Hz) | 1350 |
|  |  |  | 6.99(1H, s) | 1245 |
|  |  |  | 7.02(1H, d, J=10Hz) | 1215 |
|  |  |  | 7.24–7.42(12H, m) | 1165 |
|  |  |  |  | 1030 |
| 4(c) | —POM | —CH₃ | 1.22(9H, s) | 1770 |
|  |  |  | 1.80(2H, bs) | 1750 |
|  |  |  | 3.54(1H, d, J=18Hz) | 1575 |
|  |  |  | 3.77(3H, s) | 1350 |
|  |  |  | 3.84(1H, d, J=18Hz) | 1215 |
|  |  |  | 4.82(1H, d, J=5Hz) | 1160 |
|  |  |  | 5.01(1H, d, J=5Hz) |  |
|  |  |  | 5.87(1H, d, J=5Hz) |  |
|  |  |  | 5.94(1H, d, J=5Hz) |  |
|  |  |  | 6.02(1H, d, J=10Hz) |  |
|  |  |  | 7.04(1H, d, J=10Hz) |  |

Following the procedures and reaction conditions of Example 1(d) using the compounds obtained in Examples 2(c) to 4(c) of Table 4, there were obtained the corresponding compounds shown in Table 5.

TABLE 5

[Structure: Tr-NH-thiazole-C(=N-ODMB)-CONH-β-lactam-S-CH2-C(=)-S-CH=CH-CO2R4 with CO2R3]

| Example No. | R³ | R⁴ | NMR(CDCl₃) δ(ppm) | IR $\nu_{max}^{KBr}$ cm⁻¹ |
|---|---|---|---|---|
| 2(d) | —PMB | —CH(CH₃)₂ | 1.30(3H, d, J=6Hz) | 3340 |
|  |  |  | 1.32(3H, d, J=6Hz) | 2935 |
|  |  |  | 3.12(1H, d, J=18Hz) | 1790 |
|  |  |  | 3.60(1H, d, J=18Hz) | 1730 |
|  |  |  | 3.70(3H, s) | 1690 |
|  |  |  | 3.77(3H, s) | 1615 |
|  |  |  | 3.80(3H, s) | 1585 |
|  |  |  | 4.94(1H, d, J=5Hz) | 1515 |
|  |  |  | 5.02–5.18(1H, m) | 1465 |
|  |  |  | 5.19(1H, d, J=10Hz) | 1450 |
|  |  |  | 5.23(1H, d, J=10Hz) | 1365 |
|  |  |  | 5.27(1H, d, J=10Hz) | 1290 |
|  |  |  | 5.34(1H, d, J=10Hz) | 1220 |
|  |  |  | 5.82(1H, dd, J=5Hz, 9Hz) | 1165 |
|  |  |  | 5.92(1H, d, J=10Hz) | 1110 |

TABLE 5-continued

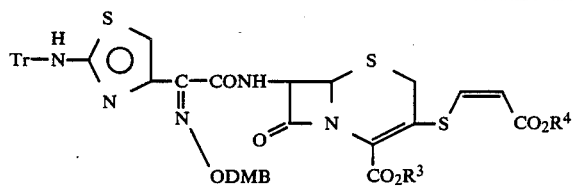

| Example No. | R³ | R⁴ | NMR(CDCl₃) δ(ppm) | IR $\nu_{max}^{KBr}$ cm⁻¹ |
|---|---|---|---|---|
| | | | 6.36–6.46(2H, m) | 1035 |
| | | | 6.85(1H, s) | |
| | | | 6.87(2H, d, J=8Hz) | |
| | | | 6.91(1H, d, J=10Hz) | |
| | | | 6.98(1H, bs) | |
| | | | 7.20–7.40(19H, m) | 3380 |
| 3(d) | —PMB | —Bh | 3.10(1H, d, J=18Hz) | 2935 |
| | | | 3.58(1H, d, J=18Hz) | 1790 |
| | | | 3.70(3H, s) | 1695 |
| | | | 3.71(3H, s) | |
| | | | 3.75(3H, s) | 1615 |
| | | | 4.93(1H, d, J=5Hz) | 1585 |
| | | | 5.14(1H, d, J=11Hz) | 1515 |
| | | | 5.23(1H, d, J=10Hz) | 1450 |
| | | | 5.24(1H, d, J=11Hz) | 1365 |
| | | | 5.33(1H, d, J=10Hz) | 1290 |
| | | | 5.71(1H, dd, J=5Hz, 9Hz) | 1250 |
| | | | 6.09(1H, d, J=10Hz) | 1210 |
| | | | 6.34–6.44(2H, m) | 1160 |
| | | | 6.81(1H, d, J=8Hz) | 1035 |
| | | | 6.84(1H, s) | |
| | | | 7.00(1H, s) | |
| | | | 7.01(1H, d, J=10Hz) | |
| | | | 7.20–7.44(30H, m) | |
| 4(d) | —POM | —CH₃ | 1.21(9H, s) | 3380 |
| | | | 3.16(1H, d, J=18Hz) | 1790 |
| | | | 3.61(1H, d, J=18Hz) | 1755 |
| | | | 3.74(3H, s) | 1700 |
| | | | 3.76(3H, s) | 1510 |
| | | | 3.79(3H, s) | 1210 |
| | | | 4.96(1H, d, J=5Hz) | 1160 |
| | | | 5.24(1H, d, J=10Hz) | |
| | | | 5.35(1H, d, J=10Hz) | |
| | | | 5.83(1H, dd, J=5Hz, 9Hz) | |
| | | | 5.90(1H, d, J=6Hz) | |
| | | | 6.04(1H, d, J=10Hz) | |
| | | | 6.41–6.46(2H, m) | |
| | | | 6.87(1H, s) | |
| | | | 6.98(1H, d, J=10Hz) | |
| | | | 6.99(1H, bs) | |
| | | | 7.20–7.38(16H, m) | |
| | | | 7.41(1H, d, J=9Hz) | |

Following the procedure and reaction conditions of Example 1(e) using the compounds obtained in Examples 2(d) to 4(d) of Table 5, there were obtained the corresponding compounds shown in Table 6.

TABLE 6

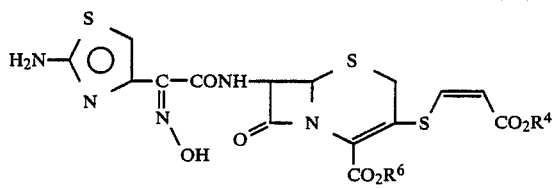

| Example No. | R⁶ | R⁴ | NMR(DMSO-d₆) δ(ppm) | IR $\nu_{max}^{KBr}$ cm⁻¹ |
|---|---|---|---|---|
| 2(e) | —Na | —CH(CH₃)₂ | 1.20(6H, d, J=6Hz) | 3415 |
| | | | 3.35(1H, d, J=17Hz) | 2980 |
| | | | 3.88(1H, d, J=17Hz) | 1770 |
| | | | 4.81–5.00(1H, m) | 1765 |
| | | | 5.06(1H, d, J=5Hz) | 1615 |
| | | | 5.63(1H, dd, J=5Hz, 8Hz) | 1535 |
| | | | 5.78(1H, d, J=10Hz) | 1375 |
| | | | 6.64(1H, s) | 1350 |
| | | | 7.13(2H, bs) | 1230 |

TABLE 6-continued

| Example No. | $R^6$ | $R^4$ | NMR(DMSO-$d_6$) $\delta$(ppm) | IR $\nu_{max}^{KBr}$ cm$^{-1}$ |
|---|---|---|---|---|
| | | | 7.40(1H, d, J=10Hz) | 1175 |
| | | | 9.44(1H, d, J=8Hz) | 1105 |
| | | | 11.37(1H, s) | 1045 |
| 3(e) | —Na | —Na | (measured solvent; D$_2$O) | 3430 |
| | | | 3.58(1H, d, J=17Hz) | 1760 |
| | | | 3.96(1H, d, J=17Hz) | 1680 |
| | | | 5.32(1H, d, J=5Hz) | 1615 |
| | | | 5.88(1H, d, J=5Hz) | 1395 |
| | | | 5.95(1H, d, J=10Hz) | 1355 |
| | | | 6.87(1H, d, J=10Hz) | 1305 |
| | | | 7.02(1H, s) | 1205 |
| | | | | 1135 |
| | | | | 1045 |
| 4(e) | —POM | —CH$_3$ | 1.15(9H, s) | 3360 |
| | | | 3.66(3H, s) | 1790 |
| | | | 3.76(1H, d, J=18Hz) | 1755 |
| | | | 4.11(1H, d, J=18Hz) | 1530 |
| | | | 5.24(1H, d, J=5Hz) | 1365 |
| | | | 5.81(1H, d, J=6Hz) | 1225 |
| | | | 5.85(1H, dd, J=5Hz, 9Hz) | 1170 |
| | | | 5.89(1H, d, J=6Hz) | 1110 |
| | | | 6.06(1H, d, J=10Hz) | |
| | | | 6.66(1H, s) | |
| | | | 7.14(2H, bs) | |
| | | | 7.51(1H, d, J=10Hz) | |
| | | | 9.52(1H, d, J=9Hz) | |
| | | | 11.33(1H, s) | |

What is claimed is:

1. A cephalosporin derivative represented by the formula

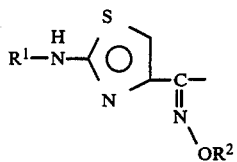

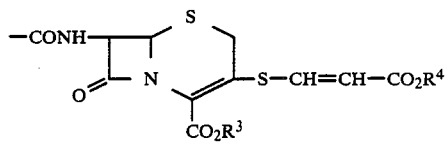

wherein $R^1$ is a hydrogen atom or a protecting group of the amino group, $R^2$ is a hydrogen atom or a protecting group of the hydroxyl group, $R^3$ is a hydrogen atom or a protecting group of the carboxyl group, and $R^4$ is a hydrogen atom or an alkyl group having 1 to 4 carbon atoms, and the non-toxic salts thereof.

* * * * *

UNITED STATES PATENT AND TRADEMARK OFFICE
CERTIFICATE OF CORRECTION

PATENT NO. : 4,937,332

DATED : June 26, 1990

INVENTOR(S) : YOKOO et al

It is certified that error appears in the above-identified patent and that said Letters Patent is hereby corrected as shown below:

Col. 5, line 11, "$R^1$" should read --$R^5$--.

Signed and Sealed this

Seventeenth Day of September, 1991

Attest:

HARRY F. MANBECK, JR.

*Attesting Officer*    *Commissioner of Patents and Trademarks*